US012702701B2

(12) United States Patent
Haeberle

(10) Patent No.: US 12,702,701 B2
(45) Date of Patent: Aug. 11, 2026

(54) COMPOSITIONS AND METHODS FOR TREATING GRANULOMATOSIS WITH POLYANGIITIS

(71) Applicant: Canem Holdings, LLC, Franklin, TN (US)

(72) Inventor: Adam Haeberle, Moorpark, CA (US)

(73) Assignee: Canem Holdings, LLC, Franklin, TN (US)

( * ) Notice: Subject to any disclaimer, the term of this patent is extended or adjusted under 35 U.S.C. 154(b) by 468 days.

(21) Appl. No.: 17/818,934

(22) Filed: Aug. 10, 2022

(65) Prior Publication Data

US 2023/0241189 A1 Aug. 3, 2023

Related U.S. Application Data

(63) Continuation of application No. 15/017,534, filed on Feb. 5, 2016, now Pat. No. 11,446,366.

(60) Provisional application No. 62/112,605, filed on Feb. 5, 2015.

(51) Int. Cl.

| | |
|---|---|
| ***A61K 38/57*** | (2006.01) |
| ***A61K 31/37*** | (2006.01) |
| ***A61K 31/40*** | (2006.01) |
| ***A61K 31/433*** | (2006.01) |
| ***A61K 38/06*** | (2006.01) |
| ***A61K 38/07*** | (2006.01) |
| ***A61K 38/08*** | (2019.01) |
| ***A61K 38/55*** | (2006.01) |
| ***A61K 45/06*** | (2006.01) |
| ***A61P 9/00*** | (2006.01) |
| ***A61P 43/00*** | (2006.01) |
| ***C07K 16/40*** | (2006.01) |
| *A61K 48/00* | (2006.01) |

(52) U.S. Cl.

CPC .............. *A61K 38/57* (2013.01); *A61K 31/37* (2013.01); *A61K 31/40* (2013.01); *A61K 31/433* (2013.01); *A61K 38/06* (2013.01); *A61K 38/07* (2013.01); *A61K 38/08* (2013.01); *A61K 38/55* (2013.01); *A61K 45/06* (2013.01); *A61P 9/00* (2018.01); *A61P 43/00* (2018.01); *C07K 16/40* (2013.01); *A61K 48/00* (2013.01)

(58) Field of Classification Search

CPC ..................................................... A61K 38/57

See application file for complete search history.

(56) References Cited

U.S. PATENT DOCUMENTS

| | | | |
|---|---|---|---|
| 11,446,366 B2 * | 9/2022 | Haeberle .............. | A61K 31/433 |
| 2013/0059289 A1 | 3/2013 | Wilson | |
| 2014/0228301 A1 | 8/2014 | Meade | |

FOREIGN PATENT DOCUMENTS

| | | |
|---|---|---|
| EP | 1071806 B1 | 6/2004 |
| WO | WO 1999/55564 | 11/1999 |
| WO | WO 2013/098672 | 7/2013 |
| WO | WO 2014/128257 | 8/2014 |

OTHER PUBLICATIONS

Korkmaz, B., et al. Neutrophil proteinase 3 and dipeptidyl peptidase I (cathespin C) as pharmacological targets in granulomatosis with polyangiitis (Wegener granulomatosis). Semin. Immunopathol., 2013, Vo., 35, p. 411-421.

Masuyama et al., Pulse methylprednisolone therapy in the treatment of Wegener's granulomatosis, vol. 20 , 2017, pp. 39-45.

Pervakova et al., The Diagnostic Value of alpha-1-antitrypsin phenotype in patients with granulomatosis with polyangiitis, Int. Journal of Rheumatology, 2016, Article ID 7831410, pp. 1-5.

Jégot, Gwenhael et al. "A substrate-based approach to convert SerpinB1 into a specific inhibitor of proteinase 3, the Wegener's granulomatosis autoantigen." FASEB journal : official publication of the Federation of American Societies for Experimental Biology vol. 25,9 (2011): 3019-31. doi:10.1096/fj.10-176552.

Perez et al. Letter to the Editor (case report), Successful a1-antitrypsin replacement therapy in a patient with a1-antiotrypsin deficiency and granulomatosis with polyangiitis, Rheumatology Advance Access published Aug. 25, 2012, pp. 1-3.

PCT/US16/16897 International Search Report and Written Opinion, mailed May 3, 2016.

Mukhtar et al., EULAR recommendations for the management of primary small and medium vessel vasculitis, Ann Rheum Dis., vol. 68, 2009, pp. 310-317.

Savage et al., Autoantibodies Developing to Myeloperoxidase and Proteinase 3 in Systemic Vasculitis Stimulate Neutrophil Cytotoxicity Toward Cultured Endothelial Cells., American Journal of Pathology, vol. 141, No. 2, Aug. 1992.

Salama et al., Animal models of ANCA associated vasculitis., Curr Opin Rheumatol. Jan. 2012; 24(1): 1-7.

Rooney, C.P., et al. Anti-proteinase 3 antibody activation of neutrophils can be inhibited by alpha1-antitrypsin. Am. J. Respir. Cell Mol. Biol., 2001, 24:747-754.

Morris et al., ANCA-associated vasculitis is linked to carriage of the Z allele of a 1 antitrypsin and its polymers, Ann Rheum Dis, vol. 70, 2011, pp. 1851-1856.

(Continued)

*Primary Examiner* — Prema M Mertz

(74) *Attorney, Agent, or Firm* — Morgan, Lewis & Bockius LLP

(57) ABSTRACT

The present specification disclose methods and uses for the treatment of a vasculitic syndrome. The disclosed methods comprise administering a composition comprising a Proteinase 3 (PR3) inhibitor to a patient in need thereof. Also disclosed are compositions comprising a PR3 inhibitor disclosed herein for use in the treatment of a vasculitic syndrome as well as use of a composition comprising a PR3 inhibitor disclosed herein in the treatment of a vasculitic syndrome. The present specification also discloses use of a composition comprising a PR3 inhibitor disclosed herein in the manufacture of a medicament for the treatment of a vasculitic syndrome.

13 Claims, 1 Drawing Sheet

Specification includes a Sequence Listing.

(56) References Cited

OTHER PUBLICATIONS

Cyril et al., Anti-proteinase 3 antibody activation of neutrophils can be inhibited by A 1-antitrypsin, Am. J. Respir. Cell Mol. Biol., vol. 24, 2001, pp. 747-754.
Geetha et al., Current therapy of granulomatosis with polyangiitis and microscopic polyangiitis: the role of rituximab, J. Nephrol, vol. 28, 2015, pp. 17-27.
Walsh et al., Effects of duration of glucocorticoid therapy on relapse rate in antineutrophil cytoplasmic antibody-associated vasculitis: a meta-analysis, Arthritis Care Res, vol. 62, 2010, pp. 1166-1173.
Ying, Q L, and S R Simon. "Kinetics of the inhibition of proteinase 3 by elafin." American journal of respiratory cell and molecular biology vol. 24,1 (2001): 83-89. doi:10.1165/ajrcmb.24.1.4300.

* cited by examiner

1 Untreated Control
2 Culture treated with 33 ng PR3
3 Culture treated with100 ng pro-IL-1β
4 Culture treated with 33 ng PR3 and 100 ng pro-IL-1β
5 Culture treated with 33 ng PR3, 100 ng pro-IL-1β and 500 ng/mL A1PI
6 Culture treated with 33 ng PR3, 100 ng pro-IL-1β and 1,000 ng/mL A1PI
7 Culture treated with 33 ng PR3, 100 ng pro-IL-1β and 2,000 ng/mL A1PI

SEQUENCE LISTING

```
Sequence total quantity: 15
SEQ ID NO: 1            moltype = AA  length = 418
FEATURE                 Location/Qualifiers
source                  1..418
                        mol_type = protein
                        organism = Homo sapiens
SEQUENCE: 1
MPSSVSWGIL LLAGLCCLVP VSLAEDPQGD AAQKTDTSHH DQDHPTFNKI TPNLAEFAFS  60
LYRQLAHQSN STNIFFSPVS IATAFAMLSL GTKADTHDEI LEGLNFNLTE IPEAQIHEGF  120
QELLRTLNQP DSQLQLTTGN GLFLSEGLKL VDKFLEDVKK LYHSEAFTVN FGDTEEAKKQ  180
INDYVEKGTQ GKIVDLVKEL DRDTVFALVN YIFFKGKWER PFEVKDTEEE DFHVDQVTTV  240
KVPMMKRLGM FNIQHCKKLS SWVLLMKYLG NATAIFFLPD EGKLQHLENE LTHDIITKFL  300
ENEDRRSASL HLPKLSITGT YDLKSVLGQL GITKVFSNGA DLSGVTEEAP LKLSKAVHKA  360
VLTIDEKGTE AAGAMFLEAI PMSIPPEVKF NKPFVFLMIE QNTKSPLFMG KVVNPTQK    418

SEQ ID NO: 2            moltype = AA  length = 379
```

-continued

```
FEATURE                Location/Qualifiers
source                 1..379
                       mol_type = protein
                       organism = Homo sapiens
SEQUENCE: 2
MEQLSSANTR FALDLFLALS ENNPAGNIFI SPFSISSAMA MVFLGTRGNT AAQLSKTFHF  60
NTVEEVHSRF QSLNADINKR GASYILKLAN RLYGEKTYNF LPEFLVSTQK TYGADLASVD  120
FQHASEDARK TINQWVKGQT EGKIPELLAS GMVDNMTKLV LVNAIYFKGN WKDKFMKEAT  180
TNAPFRLNKK DRKTVKMMYQ KKKFAYGYIE DLKCRVLELP YQGEELSMVI LLPDDIEDES  240
TGLKKIEEQL TLEKLHEWTK PENLDFIEVN VSLPRFKLEE SYTLNSDLAR LGVQDLFNSS  300
KADLSGMSGA RDIFISKIVH KSFVEVNEEG TEAAAATAGI ATFCMLMPEE NFTADHPFLF  360
FIRHNSSGSI LFLGRFSSP                                               379

SEQ ID NO: 3           moltype = AA  length = 11
FEATURE                Location/Qualifiers
source                 1..11
                       mol_type = protein
                       organism = Homo sapiens
SEQUENCE: 3
GIATFCMLMP E                                                       11

SEQ ID NO: 4           moltype = AA  length = 11
FEATURE                Location/Qualifiers
REGION                 1..11
                       note = SerpinB1 Modified RCL
source                 1..11
                       mol_type = protein
                       organism = synthetic construct
SEQUENCE: 4
GIATDCMLMP E                                                       11

SEQ ID NO: 5           moltype = AA  length = 12
FEATURE                Location/Qualifiers
REGION                 1..12
                       note = SerpinB1 Modified RCL
source                 1..12
                       mol_type = protein
                       organism = synthetic construct
SEQUENCE: 5
GIATDCRMLM PE                                                      12

SEQ ID NO: 6           moltype = AA  length = 11
FEATURE                Location/Qualifiers
REGION                 1..11
                       note = SerpinB1 Modified RCL
source                 1..11
                       mol_type = protein
                       organism = synthetic construct
SEQUENCE: 6
GIATDARLMP E                                                       11

SEQ ID NO: 7           moltype = AA  length = 11
FEATURE                Location/Qualifiers
REGION                 1..11
                       note = SerpinB1 Modified RCL
source                 1..11
                       mol_type = protein
                       organism = synthetic construct
SEQUENCE: 7
GDATDARLMP E                                                       11

SEQ ID NO: 8           moltype = AA  length = 11
FEATURE                Location/Qualifiers
REGION                 1..11
                       note = SerpinB1 Modified RCL
source                 1..11
                       mol_type = protein
                       organism = synthetic construct
SEQUENCE: 8
GISTDARLMP E                                                       11

SEQ ID NO: 9           moltype = AA  length = 117
FEATURE                Location/Qualifiers
source                 1..117
                       mol_type = protein
                       organism = Homo sapiens
SEQUENCE: 9
MRASSFLIVV VFLIAGTLVL EAAVTGVPVK GQDTVKGRVP FNGQDPVKGQ VSVKGQDKVK  60
AQEPVKGPVS TKPGSCPIIL IRCAMLNPPN RCLKDTDCPG IKKCCEGSCG MACFVPQ     117
```

-continued

```
SEQ ID NO: 10          moltype = AA  length = 6
FEATURE                Location/Qualifiers
REGION                 1..6
                       note = Trappin-2 Motif
source                 1..6
                       mol_type = protein
                       organism = synthetic construct
SEQUENCE: 10
GQDPVK                                                                6

SEQ ID NO: 11          moltype = AA  length = 256
FEATURE                Location/Qualifiers
source                 1..256
                       mol_type = protein
                       organism = Homo sapiens
SEQUENCE: 11
MAHRPPSPAL ASVLLALLLS GAARAAEIVG GHEAQPHSRP YMASLQMRGN PGSHFCGGTL  60
IHPSFVLTAA HCLRDIPQRL VNVVLGAHNV RTQEPTQQHF SVAQVFLNNY DAENKLNDVL  120
LIQLSSPANL SASVATVQLP QQDQPVPHGT QCLAMGWGRV GAHDPPAQVL QELNVTVVTF  180
FCRPHNICTF VPRRKAGICF GDSGGPLICD GIIQGIDSFV IWGCATRLFP DFFTRVALYV  240
DWIRSTLRRV EAKGRP                                                   256

SEQ ID NO: 12          moltype = AA  length = 6
FEATURE                Location/Qualifiers
REGION                 1..6
                       note = Azapeptide
source                 1..6
                       mol_type = protein
                       organism = synthetic construct
SEQUENCE: 12
VADCAQ                                                                6

SEQ ID NO: 13          moltype = AA  length = 8
FEATURE                Location/Qualifiers
REGION                 1..8
                       note = Azapeptide
source                 1..8
                       mol_type = protein
                       organism = synthetic construct
SEQUENCE: 13
VADCRDRQ                                                              8

SEQ ID NO: 14          moltype = AA  length = 6
FEATURE                Location/Qualifiers
REGION                 1..6
                       note = Azapeptide
source                 1..6
                       mol_type = protein
                       organism = synthetic construct
SEQUENCE: 14
VAECCQ                                                                6

SEQ ID NO: 15          moltype = AA  length = 11
FEATURE                Location/Qualifiers
REGION                 1..11
                       note = Azapeptide
source                 1..11
                       mol_type = protein
                       organism = synthetic construct
SEQUENCE: 15
QPMDVVQSVP Q                                                          11
```

COMPOSITIONS AND METHODS FOR TREATING GRANULOMATOSIS WITH POLYANGIITIS

CROSS-REFERENCES TO RELATED APPLICATIONS

This patent application is a continuation of U.S. patent application Ser. No. 15/017,534, filed Feb. 5, 2016, which claims the right of priority pursuant to 35 U.S.C. § 119 (e) and is entitled to the benefit of the filing date of U.S. Provisional Patent Application 62/112,605, filed on Feb. 5, 2015, the contents of which are hereby expressly incorporated by reference in their entirety.

REFERENCE TO SEQUENCE LISTING

The instant application contains a Sequence Listing which has been submitted electronically in XML file format and is hereby incorporated by reference in its entirety. Said XML file format, created on Aug. 9, 2022, is named 008073-5233-US01_Sequence_Listing.xml and is 18,871 bytes in size.

BACKGROUND

Granulomatosis with Polyangiitis (GPA or Wegener's Granulomatosis) is a rare incurable form of vasculitis (inflammation of blood vessels) that affects the nose, lungs, kidneys, and other organs. GPA is characterized by blood vessel inflammation (vasculitis). In GPA, organ damage occurs as a result of inflammation in vasculitis involving the small- and medium-sized blood vessels, and from a type of tissue injury called granulomatous inflammation. A granuloma is a type of inflammation that can usually be seen on biopsies of affected organs.

Per the American College of Rheumatology homepage, 3 out of every 100,000 people in the United States are affected with GPA. By published reports, incidence in the US is estimated to be as high as 8.6 per 1,000,000 or 2580 new cases per year. Prevalence in the US is estimated account for between 26 and 90 treated cases per 1,000,000 per year or greater than 7800 cases per year (Watts R, Epidemiology of Systemic Vasculitis, 1995). The disease is difficult to diagnose and currently available treatments are inadequate.

Most commonly, GPA affects the sinuses, lungs and kidneys, but also can affect the eyes, ears, skin, nerves, joints and other organs. Because of the variety of potential organ involvement, a wide range of symptoms can develop over days to months. For 90% of people, the first symptoms appear in the respiratory tract (e.g., nose, sinuses and lungs) and include nasal congestion, frequent nosebleeds, shortness of breath, and cough that may produce bloody phlegm. Other early symptoms can include joint pain, decreased hearing, skin rashes, eye redness and/or vision changes, fatigue, fever, appetite and weight loss, night sweats, and numbness or loss of movement in the fingers, toes or limbs.

Currently available treatment options for GPA are inadequate with patients experiencing decreased life expectancy and decreased quality of life. In addition, the available treatments for GPA all have ongoing safety issues and work on the same general principle of suppressing the body's reactive response and immune system. Chronic therapy with glucocorticoids lead to multiple syndromes in of itself. Only half the patients treated with Rituximab in flare have a positive response to treatment and multiple key opinion leaders have raised questions on the justification of repeat dosing with Rituximab. In the pivotal study of Rituximab in the treatment of GPA, the number and severity of adverse events were not deemed significantly different between Rituximab and Cyclophosphamide (CYC, a highly toxic immunosuppressant agent, leading to sterility, kidney problems etc.). While this can be effective in saving the life of the patient these treatments are not without their own safety and quality of life issues; further they do not address the cause of the disease itself. There is a current unmet need for treatments of equal or greater effectiveness that have an increased safety profile. Long term chronic dosing with A1PI has been shown in a large population to be safe with a benign adverse event profile. The greatest challenges in the management of GPA are the maintenance of disease remission and the avoidance of treatment-related morbidity and mortality.

Additionally, greater than 70% of PR3 positive GPA patients will relapse and while Rituximab has been approved for treatment of the indication it is the opinion of medical leaders in the rheumatology field that this has shifted the needs of patients rather than eliminating them.

Accordingly, there is a need for a new effective treatment of GPA which avoids the long-term side effects obtained with the currently available therapies and focuses on treatment of the underlying condition rather than suppressing the immune system.

SUMMARY

Aspects of the present specification disclose methods for treating a vasculitic syndrome. The disclosed methods comprise administering a composition comprising a Proteinase 3 (PR3) inhibitor to a patient in need thereof. A PR3 inhibitor may be a protein, a polypeptide fragment thereof or a variant thereof or small molecule. Non-limiting examples of a PR3 inhibitor disclosed herein include a α-1 Protease Inhibitor (A1PI), a Serpin B1, a Trappin-2, an elafin, a Eglin c, a modified α-1 antichymotrypsin, a α-12 macroglobulin, an azapeptide, a PR3 antibody or antibody fragment thereof, a 1,2,5-thiadiazolidin-3-one 1,1 dioxide derivative, an N-hydroxysuccinimide derivative, 7-NH$_2$-4-CI-3-(2-bromoethoxy)isocoumarin, 3,4-dichloroisocoumarin, MeO-Suc-Ala-Ala-Pro-Val$^P$(OPh)$_2$, Boc-Val-Pro-ValP(OPh)$_2$, MeO-Suc-Ala-Ala-Pro-ValCh$_2$CI, or SURAMIN™. A vasculitic syndrome includes, without limitation, granulomatosis with polyangiitis (GPA or Wegener's Granulomatosis), small vessel vasculitides, microscopic polyangiitis, pauci-immune crescentic glomerulonephritis, Churg-Strauss syndrome, drug induced vasculitides, cystic fibrosis, inflammatory bowel disease, primary sclerosing cholangitis, rheumatoid arthritis, autoimmune liver disease, drug induced syndromes and parasitic infections.

Other aspects of the present specification disclose compositions comprising a PR3 inhibitor disclosed herein for use in the treatment of a vasculitic syndrome disclosed herein.

Other aspects of the present specification disclose use of a composition comprising a PR3 inhibitor disclosed herein in the treatment of a vasculitic syndrome disclosed herein.

Other aspects of the present specification disclose use of a composition comprising a PR3 inhibitor disclosed herein in the manufacture of a medicament for the treatment of a vasculitic syndrome disclosed herein.

Other aspects of the present specification disclose a kit comprising a PR3 inhibitor.

DETAILED DESCRIPTION

Figures 1A, 1B, 1C:
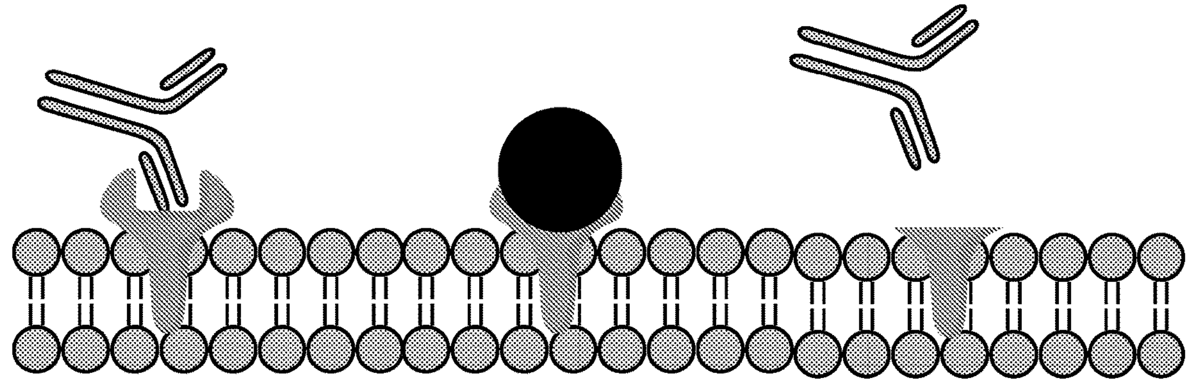
FIG. 1A-C depict the cell surface of the neutrophil with the exposed and activated PR3 receptor. Without A1PI, ANCA binds the PR3 receptor (FIG. 1A). Exogenous A1PI cleaves the active domain from the PR3 receptor (FIG. 1B) which removes the ability of ANCA to bind to the receptor and activate the neutrophil (FIG. 1C).

The present disclosure accordingly addresses the need for a new, effective therapy for GPA, which directly addresses the disease mechanism of action avoids both the short and long-term side-effects obtained with the present therapies.

GPA is part of a larger group of vasculitic syndromes, all of which feature an autoimmune attack by an abnormal type of circulating antibodies termed ANCA (anti-neutrophil cytoplasmic antibodies) against small and medium-size blood vessels. ANCA can be divided into four patterns when visualized by immunofluorescence: cytoplasmic ANCA (c-ANCA), C-ANCA (atypical), perinuclear ANCA (p-ANCA) and atypical ANCA (a-ANCA), also known as x-ANCA. ANCAS are associated with small vessel vasculitides including granulomatosis with polyangiitis (previously known as Wegener's granulomatosis), microscopic polyangiitis, primary pauci-immune necrotizing crescentic glomerulonephritis (a type of renal-limited microscopic polyangiitis), Churg-Strauss syndrome and drug induced vasculitides. Proteinase 3 (PR3) directed c-ANCA is present in 80-90% of granulomatosis with polyangiitis, 20-40% of microscopic polyangiitis, 20-40% of pauci-immune crescentic glomerulonephritis and 35% of Churg-Strauss syndrome. c-ANCA (atypical) is present in 80% of cystic fibrosis (with BPI as the target antigen) and also in inflammatory bowel disease, primary sclerosing cholangitis and rheumatoid arthritis (with antibodies to multiple antigenic targets). p-ANCA with MPO specificity is found in 50% of microscopic polyangiitis, 50% of primary pauci-immune necrotizing crescentic glomerulonephritis and 35% of Churg-Strauss syndrome. p-ANCA with specificity to other antigens are associated with inflammatory bowel disease, rheumatoid arthritis, drug-induced vasculitis, autoimmune liver disease, drug induced syndromes and parasitic infections. Atypical ANCA is associated with drug-induced systemic vasculitis, inflammatory bowel disease and rheumatoid arthritis.

PR3 is a serine protease displayed on the membrane surface of both quiescent and activated neutrophils. Neutrophils isolated from GPA patients have increased cell-surface PR3 compared to non-GPA patients. This increase in surface PR3 occurs in both individuals with severe A1PI deficiency and patients with normal levels of circulating A1PI. As mentioned above, GPA is characterized by an autoimmune attack by ANCA. In GPA, circulating c-ANCA bind PR3 surface of neutrophils. ANCA binding activates these neutrophils leading them to attack and damage blood vessels.

Alpha-One Proteinase Inhibitor ("A1PI"; aka "Alpha 1 antitrypsin," "AlAT," "Alpha-1-antiproteinase," or "Serpin A1") is a physiologic inhibitor of PR3. Exogenous A1PI cleaves the active domain from the PR3 receptor on the cell surface of a neutrophil. This cleavage of the PR3 receptor prevents the binding of cytoplasmic ANCA (c-ANCA) to the PR3 receptor, thereby preventing the FcγR11 a cross-linkage required for neutrophil cell activation. Neutrophils isolated from GPA patients have been studied in-vitro and it was confirmed that A1PI can block binding and activation of neutrophils by anti-PR3 IgG in both healthy adults and GPA patients. While there have been numerous reports noting the increased incidence of GPA in the Alpha 1 Trypsin Deficient (AATD) population no one has moved beyond this to test the potential of the compound as a treatment for the disease irrespective of circulating levels of A1PI.

Most GPA patients do not have a decreased amount of endogenous A1 Pl. That said, subjects having a decreased amount of endogenous A1PI may be at increased risk of GPA. Thus, subjects having either of the S or Z alleles of the A1PI gene may be considered to be in a population more likely to have GPA or at risk of developing GPA. The risk is elevated in patients with either the homozygous (ZZ or SS) or compound homozygous (SZ) genotypes, although there is a smaller risk of GPA in patients carrying one copy of either S or Z allele. (Mahr et al. Arthritis Rehem. 2010 December; 62 (12): 3760-3767).

However, although there is an increased risk, not all subjects with an endogenous A1PI deficiency develop GPA. Thus, the key feature of GPA diagnosis and suitability for administration of the present compositions is the presence of c-ANCA in the subject and not A1PI genotype.

Thus, the methods contemplate herein disclose the use of an inhibitor of PR3 or PR3 inhibitor. A PR3 inhibitor is an agent which inhibits the physiological function of PR3 such as by binding PR3, by decreasing, preventing or inhibiting the binding of c-ANCA to PR3, or which prevents PR3 activated degranulation from neutrophils. A PR3 inhibitor may be a reversible PR3 inhibitor or irreversible PR3 inhibitor. A reversible PR3 inhibitor is a composition with an active ingredient that has an affinity for PR3 via non-covalent interactions. An irreversible PR3 inhibitor interact using stable, covalent interactions with PR3. A PR3 inhibitor may be a non-specific PR3 inhibitor or a specific PR3 inhibitor. In particular, many non-specific PR3 inhibitors are also inhibitors of Human Neutrophil Elastase (HNE), and sometimes cathepsin G (CG). A PR3 inhibitor includes, without limitation, A1PI, elafin, pre-elafin (i.e., Trappin-2), Serpin B1, a-2 macroglobulins, α-2 macroglobulin, Eglin C, a modified α-1 Antichymtrypsin (ACT), azapeptides, and antibodies to PR3.

The present methods also contemplate the use of an agent to remove the domain of PR3 that the body is recognizing for the production of auto-antibodies. By removing the target the concentration of ANCA may decrease due to lack of stimulus to the immune system's b-cells.

Inhibitors of PR3 include but are not limited to: proteins, peptides antibodies and fragments thereof which selectively bind PR3, and small molecules. Examples of proteins for use herein include A1PI, Serpin B1, Trappin-2, Elafin, α-2 macroglobulin, modified α-1 antichymotrypsin, eglin c, azapeptides, and fragments and variants thereof. A "small molecule" compound for use herein may be, for instance, a 1,2,5-thiadiazolidin-3-one 1,1 dioxide derivative, an N-hydroxysuccinimide derivative, 7-$NH_2$-4-CI-3-(2-bromoethoxy)isocoumarin, 3,4-dichloroisocoumarin, MeO-Suc-Ala-Ala-Pro-$Val^P(OPh)_2$, Boc-Val-Pro-$Val^P(OPh)_2$, MeO-Suc-Ala-Ala-Pro-$ValCh_2Cl$, and SURAMIN™.

A modified protein or a "variant" of a protein as described herein is a protein having one or more amino acid additions, deletions, or substitutions. As discussed below, these additions, deletions, or substitutions may be conservative or non-conservative. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The most commonly occurring exchanges are Ala/Ser, Val/Ile, Asp/Glu, Thr/Ser, Ala/Gly, Ala/Thr, Ser/Asn, AlaNal, Ser/Gly, Ala/Pro, Lys/Arg, Asp/Asn, Leu/Ile, LeuNal, Ala/Glu and Asp/Gly, in both directions. Amino acid exchanges in proteins and peptides, which do not generally alter the activity of the proteins or peptides, are known in the art (H. Neurath, R. L. Hill, The Proteins, Academic Press, New York, 1979).

The term "derivative of a protein" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

Variants may be characterized by either sequence identity or the number of amino acid additions, deletions, or substitutions. Fragments or isoforms of the proteins discussed herein may include amino acid additions, deletions, or substitutions, which again, may be characterized by sequence identity or number of amino acid changes.

The term "sequence homology" or "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89:10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48:443), as revised by Smith and Waterman (Adv. Appl. Math., 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12:387) BLASTP, BLASTN and FASTA (Altschul et al., J. Molec. Biol., 1990: 215: 403). In one aspect the present modified sequence variants have at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with another sequence, either on a local or a full-length basis.

If on a local basis, the locality is determined by a region of the non-modified or native sequence, or a specifically identified motif of non-modified or native sequence. In one aspect the locality is at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, or at least 75 nucleic acids or amino acids of the non-modified or native sequence.

In an embodiment, a PR3 inhibitor is A1PI or a variant thereof. A1PI is a serpin (gene "Serpin A1"). A1PI has three isoforms, the first being the 418 amino acid sequence of SEQ ID NO: 1. The second being amino acids 1-359 of SEQ ID NO: 1 with the addition of VRSP at the C-terminal, and the third isoform being a sequence having amino acids 1-306 of SEQ ID NO: 1. The signal peptide in the A1PI sequences is amino acids 1-24 of SEQ ID NO: 1. Glycosylation when expressed in human occurs at amino acid positions 70 (N-linked), 107 (N-linked) and 271 (N-linked). A S-cysteinyl cysteine may occur at amino acid position 256 of SEQ ID NO: 1. AIPI is sold in intravenous formulations as ZEMAIRA™ (CSL Behring), ARALAST™ (BAXTER), ARALAST NP™ (BAXTER), GLASSIA™ (Baxter), PROLASTIN™ (Grifols Therapeutics), PROLASTIN-C™ (Grifols Therapeutics).

In aspects of this embodiment, a PR3 inhibitor is an A1PI having an amino acid sequence of SEQ ID NO: 1 with the addition of VRSP at the C-terminal, or amino acids 1-306 of SEQ ID NO: 1. In other aspects of this embodiment, a PR3 inhibitor is an A1PI having an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 1, amino acids 1-359 of SEQ ID NO: 1 with the addition of VRSP at the C-terminal, or amino acids 1-306 of SEQ ID NO: 1. In yet other aspects of this embodiment, a PR3 inhibitor is an A1PI having an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 1, amino acids 1-359 of SEQ ID NO: 1 with the addition of VRSP at the C-terminal, or amino acids 1-306 of SEQ ID NO: 1.

In other aspects of this embodiment, a PR3 inhibitor is an A1PI having, e.g., at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 1, amino acids 1-359 of SEQ ID NO: 1 with the addition of VRSP at the C-terminal, or amino acids 1-306 of SEQ ID NO: 1. In yet other aspects of this embodiment, a PR3 inhibitor is an A1PI having, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or noncontiguous amino acid deletions, additions, and/or substitutions relative to SEQ ID NO: 1, amino acids 1359 of SEQ ID NO: 1 with the addition of VRSP at the C-terminal, or amino acids 1-306 of SEQ ID NO: 1.

In still other aspects of this embodiment, a PR3 inhibitor is an A1PI having the following amino acid changes to SEQ ID NO: 1: S4L, amino acid 12 may be deleted, L23P, D26H, D26A, T37A, H39L, A58T, L61P, R63C, L65P, S69F, Amino acid 75 may be missing, S75F, A84T, G91E, T92I, T96A, T109M, P112T, 1116N, R125H, G139S, G139D and N140G, G172R, G172W, Q180E, T174H, amino acids 190-198 change from QGKIVDVLK to GFQNAILVR, E228K, E229D, V237A, T273N, D280V, D280G, E288V, amino acid 305 may be deleted, V326I, S354F, A360T, D365N, E366K, M382R, P386H, P386T, E387K, P393L, E400D, G410L, N414S, and P415H.

In an embodiment, a PR3 inhibitor is Serpin B1 or a variant thereof. Serpins are irreversible suicide inhibitors of serine proteases. Serpins interact with their target by a mechanism involving cleavage of the reactive center loop (RCL) of the serpin between the P1 and P1' residue and its complete insertion into the A sheet of the serpin which results into pole-to-pole displacement of the covalently bound protease within the complex. (Jegot et al., FASEB J., 25:3019-3031, 2011). Binding the modified Serpin B1 to activated neutrophils demonstrated a decrease of binding between PR3 and ANCA. (Jegot et al., FASEB J., 25:3019-3031, 2011). Serpin B1 is a 379 amino acid sequence of SEQ ID NO: 2. Serpin B1 RCL is an amino acid segment of Serpin B1 located at residues 339-349 of SEQ ID NO: 2 and having the amino acid sequence GIATFCMLMPE (SEQ ID NO: 3).

In aspects of this embodiment, a PR3 inhibitor is a Serpin B1 having an amino acid sequence of SEQ ID NO: 2. In other aspects of this embodiment, a PR3 inhibitor is a Serpin B1 having an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 2. In yet other aspects of this embodiment, a PR3 inhibitor is a Serpin B1 having an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 2.

In other aspects of this embodiment, a PR3 inhibitor is a Serpin B1 having, e.g., at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 2. In yet other aspects of this embodiment, a PR3 inhibitor is a Serpin B1 having, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or non-contiguous amino acid deletions, additions, and/or substitutions relative to SEQ ID NO: 2.

In another aspect of this embodiment, a serpin B1 may be modified outside the RCL, but also contains up to 1, up to 2, or up to 3 amino acid substitutions in the RCL region of SEQ ID NO: 3.

In another aspect of this embodiment, the serpin B1 may be modified at one or more of its two Functional sites: F343-C344 of SEQ ID NO: 2 (interacts with CG); and C344-M345 of SEQ ID NO: 2 (cleaved by PR3 and HNE to initiate irreversible protease binding). F343 is the P1 for reaction with CG, and is P2 for inhibiting PR3 and HNE, and reacts with protease residue 99 of PR3. In another aspect of this embodiment, F343 is substituted with asparagine (Asp) which suppresses cleavage by CG and improves cleavage by PR3. In another aspect of this embodiment, M345 is replaced with an arginine (Arg), which helps with the HNE cleavage.

In another aspect of this embodiment, the modified RCL may be any of: GIATDCMLMPE (SEQ ID NO: 4), GIATDCRMLMPE (SEQ ID NO: 5), GIATDARLMPE (SEQ ID NO: 6), GDATDARLMPE (SEQ ID NO: 7), GISTDARLMPE (SEQ ID NO: 8) (preferred inhibitor of PR3 because only slowly cleaved by HNE).

In an embodiment, a PR3 inhibitor is Trappin-2 or a variant thereof. Trappin-2 (aka "pre-elafin") is the precursor of elafin. Elafin is the mature product of Trappin-2, representing the C-terminal 57 amino acids of Trappin-2 (amino acids 61-117 of SEQ ID NO: 9). Elafin is an epithelial proteinase inhibitor and is also known as Skin-derived Anti-leukoproteinase (SKALP), peptidase inhibitor 3, or Elastase-Specific Inhibitor (ESI). Trappin-2 is 117 amino acids in length and has the amino acid sequence of SEQ ID NO: 9. Other sources include the protein sequences that are shown in GENBANK™ Accession No. NP002629, P19957, NP003055, BAA02441, JH0614, AAB34627, CAA79223 and AAB26371, as accessed on Nov. 5, 2014, and are incorporated herein by reference in their entirety. Entrez-Gene number 5266. Disulfide bonds may occur between amino acids 76 and 105, 83 and 109, 92 and 104, and 98 and 113 of SEQ ID NO: 9. Trappin-2, a protease inhibitor, has a unique N-terminal domain that enables it to become cross-linked to extracellular matrix proteins by transglutaminase. This domain (amino acids 31-47 and/or 55-71 of SEQ ID NO: 9) contains several repeated motifs (represented by this entry) with the consensus sequence Gly-Gln-Asp-Pro-Val-Lys (SEQ ID NO: 10), and these together can anchor the whole molecule to extracellular matrix proteins, such as laminin, fibronectin, beta-crystallin, collagen IV, fibrinogen, and elastin, by transglutaminase-catalysed cross-links. The whole domain is rich in glutamine and lysine, thus allowing and transglutaminase(s) to catalyse the formation of an intermolecular epsilon-(gamma-glutamyl) lysine isopeptide bond [PMID: 17964057]. The gene product pre-elafin consists of 117 amino acids: the initiator Met, a putative 22-amino acid signal peptide, a pro-sequence from amino acids 23-60 of SEQ ID NO: 9, and the C-terminal 57 amino acids for mature elafin (amino acids 61-117 of SEQ ID NO: 9).

In aspects of this embodiment, a PR3 inhibitor is a Trappin-2 having an amino acid sequence of SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9. In other aspects of this embodiment, a PR3 inhibitor is a Trappin-2 having an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9. In yet other aspects of this embodiment, a PR3 inhibitor is a Trappin-2 having an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9.

In other aspects of this embodiment, a PR3 inhibitor is a Trappin-2 having, e.g., at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids or at least 20 amino acids, contiguous and/or non-contiguous amino acid deletions, additions, and/or substitutions relative to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9. In yet other aspects of this embodiment, a PR3 inhibitor is a Trappin-2 having, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids or at most 20 amino acids, contiguous and/or non-contiguous amino acid deletions, additions, and/or substitutions relative to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9.

In one embodiment, a Trappin-2 include amino acid sequences having substitutions at amino acids 17, 34, 91, and 92 of SEQ ID NO: 9. In one embodiment, the a Trappin-2 may include up to 4, up to 3, up to 2, or up to 1 of the amino acid amino acid substitutions as follows: T17M, T34P, R91C, or C92A when compared to SEQ ID NO: 9.

The Elafin gene resides within a 700-kilobase locus on chromosome 20q13 that contain fourteen genes encoding whey acidic protein (WAP) domain proteins (e.g., amino acid positions 69-117 of SEQ ID NO: 9). Elafin itself is a WAP domain containing protein. Elafin belongs to the Trappin gene family and was given the systematic name Trappin-2 in a recent classification. The Trappin family is defined by an N-terminal transglutaminase substrate domain and a C-terminal four disulphide core. Trappins have been suggested to play a role in the regulation of inflammation and in protection against tissue damage in stratified epithelia. Elafin is an inhibitor of leukocyte elastase and proteinase-3 and in addition it is a substrate for transglutaminases. The protein is constitutively expressed in various epithelia including those of hair follicles, esophagus, vagina and oral cavity. Elafin is not present in normal human skin but is strongly induced in inflammatory conditions like psoriasis and wound healing. The full-length protein is translated as a 12.3 kDa protein of 117 amino acids termed pre-Elafin or Trappin-2. Cleavage of the signal peptide yields a mature protein with a molecular mass of 9.9 kDa. The 9.9 kDa secreted protein is the major form found in culture medium. In skin extracts a 6 kDa form comprising the 57 most C-terminal amino acids is present. In serum, both the 9.9 and the 6 kDa form appear to be present. In serum/plasma of healthy individual approximately 10-50 ng/ml of Elafin is present.

Association and dissociation rate constants for Elafin were measured to be association rate constant of 4.0×10·6 M-'s−1, dissociation rate constant of 1.7×10−3s−1, and inhibition constant of $4.2\times10^{-10}$ M. and Simon, American Journal of Respiratory Cell and Molecular Biology, V. 24, 2001, pp. 83-89, then entire contents of which are herein expressly incorporated by reference). An equilibrium dissociation constant (Ki) for proteinase-3/elafin association is 20 nM. Proteinase-3/Trappin-2 associations reportedly have a K of 12 nm. However, Ki values for both trappin and elafin have been tested to be in the sub-nanomolar range (See e.g., Nobar et al, FEBS 272 (2005) 588305893 abstract, the entire contents of which are hereby expressly incorporated by reference).

Other protein or peptide inhibitors of PR3 include Alpha-2 macroglobulin, Eglin C (Rao et al., J. Biol. Chem 1991; 266:9540-8), a modified Alpha-1 Antichymtrypsin (ACT) (Grouas et al., Biochem Biophys Res Commun 1997, 33:697-9 describing a bioengineered, recombinant variant of ACT (LEX032)), and azapeptides (Korkmaz et al., Current Pharmaceutical Design, 2013, v. 19, No. 6, pp. 96676). One example of an azapeptide of interest have structures of Abz-VADCAQ-EDDnp (SEQ ID NO: 12) and Abz-VA-DCRDRQ-EDDnp (SEQ ID NO: 13), Abz-VAECCQ-EDDnp (SEQ ID NO: 14) and Abz-QPMDVVQSVPQ-EDDnp (SEQ ID NO: 15). (EDDnp=N-(2,4-dinitrophenyl) ethylenediamine); Abz=ortho-aminobenzoic acid).

Antibodies against PR3 or fragments thereof bind to one or more epitopes of PR3. Examples of the epitope include a single amino acid sequence, a three-dimensional structure formed by an amino acid sequence, an amino acid sequence having a sugar chain bound thereto, a three-dimensional structure formed by an amino acid sequence having a sugar chain bound thereto, and the like, which a monoclonal antibody recognizes and binds to. The antibody may be polyclonal or monoclonal.

PR3 has the amino acid sequence of SEQ ID NO: 11. Amino acids 1-25 of SEQ ID NO: 11 are a signal sequence. PR3 has active sites at amino acid 71, 118, and 203 of SEQ ID NO: 11. Amino acids 26 and 27 and 249-256 of SEQ ID NO: 11 are cleaved during processing, and the mature protein includes amino acids 28-248 of SEQ ID NO: 11.

In other aspects of this embodiment, a PR3 has an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 11 or amino acids 28-248 of SEQ ID NO: 11. In yet other aspects of this embodiment, a PR3 has an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 11 or amino acids 28-248 of SEQ ID NO: 11.

In other aspects of this embodiment, a PR3 has, e.g., at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 11 or amino acids 28-248 of SEQ ID NO: 11. In yet other aspects of this embodiment, a PR3 has, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or non-contiguous amino acid deletions, additions, and/or substitutions relative to SEQ ID NO: 11 or amino acids 28-248 of SEQ ID NO: 11.

In another aspect of this embodiment, a PR3 may include up to 12, up to 11, up to 10, up to 9, up to 8, up to 7, up to 7, up to 6, up to 5, up to 4, up to 3, up to 2, or up to 1 of the amino acid amino acid deletions or substitutions of SEQ ID NO: 11 as follows: A2R, S38I, P40PI, Q46E, R48A, S64D, A70P, V119I, A135T, T136S, and/or amino acid 255 may be delete.

In another aspect of this embodiment, the antibody recognizes one or more of Lys99, Ser195, Asp102, and His57 of SEQ ID NO: 11.

An antibody which binds to PR3 with high affinity is an antibody which has enough affinity for a therapeutic antibody, preferably an antibody which binds to PR3 with dissociation constant KD value less than $1\times10^{7}$M, less than $1\times10^{8}$M, less than $1\times10^{9}$M less than $7\times10^{-10}$M, or less than $2\times10^{-10}$M in terms of affinity. Therefore, the antibody of the present invention can exhibit high therapeutic effects. In one embodiment, the antibody is slow to dissociate from PR3 binding.

In one embodiment, the epitope is a linear epitope, and the antibody or antibody fragment specifically recognizes a sequence of at least 7, at least 8, at least 9, at least 10, at least 11, at least 12, at least 13, at least 14, or at least 15 contiguous amino acids of SEQ ID NO: 11, or a sequence having at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% sequence identity to the corresponding region of SEQ ID NO: 11.

Antibodies may be complete antibodies, or portions of an antibody capable of selectively binding to PR3 and inhibiting PR3 interaction with c-ANCA or neutrophil degranulation. The term "antibody" as used herein is intended to include antibodies, immunoglobulin chains, monoclonal antibodies, polyclonal antibodies, chimeric antibodies, and antibody variants containing one or more characteristic structures of an antibody. Characteristic structures of an antibody include antibody fragments, antibody hinge regions, the Fc region, a full-length heavy chain, a full-length light chain, a variable region, a constant region, a CDR (1, 2, or 3), etc. Antibodies also include chimeric antibodies and fusion proteins. Antibody structures may be taken from immunoglobulins such as IgM, IgG, IgE, IgA, or IgD.

In addition, the present methods contemplate the administration of small molecules. A "small molecule" compound for use herein may be, for instance, a 1,2,5-thiadiazolidin-3-one 1,1 dioxide derivative, an N-hydroxysuccinimide derivative, 7-$NH_2$-4-CI-3-(2-bromoethoxy)isocoumarin, 3,4-dichloroisocoumarin, MeO-Suc-Ala-Ala-Pro-ValP$(OPh)_2$, Boc-Val-Pro-ValP$(OPh)_2$, MeO-Suc-Ala-Ala-Pro-Val$CH_2$CI, N-tosyl-L-pheylalanine-chloromethyl ketone (TPCK) and SURAMIN™. Small molecules of interest may be found in Korkmaz et al., Current Pharmaceutical Design, 2013, 19, 966-976, the entire contents of which are hereby incorporated by reference.

As used herein, the term "subject" means any mammal, and, in particular, a human, and can also be referred to, e.g., as an individual or patient. A "subject in need of treatment" for GPA according to the methods disclosed herein is a subject who has GPA, a subject having c-ANCA, or a subject that is at risk of GPA.

The primary patient population of interest is patients diagnosed with GPA (i.e., Wegener's Granulomatosis (WG)). This population is characterized by the presence of c-ANCA.

In one embodiment, the dose administered weekly ranges from 1-1000 mg/kg, 1-500 mg/kg, 1-200 mg/kg, 1-100 mg/kg, 1-50 mg/kg, 10-500 mg/kg, 10-250 mg/kg, 10-200 mg/kg, 10-150 mg/kg, 10-100 mg/kg, 10-50 mg/kg, 50-1000 mg/kg, 50-500 mg/kg, 50-250 mg/kg, 50-200 mg/kg, 50-150 mg/kg, 50-100 mg/kg, 20-500 mg/kg, 20-250 mg/kg, 20-200 m/kg, 20-150 mg/kg, 20-100 mg/kg, 60-120 mg/kg, or 20-60 mg/kg. In one embodiment, when administering the protein, for instance with A1PI, a dosage range can range from 60-240 mg/kg body weight administered once weekly. In one embodiment, A1PI is administered at 20 mg/kg, 30 mg/kg, 40 mg/kg, 50 mg/kg, 60 mg/kg, 70 mg/kg, 80 mg/kg, 90 mg/kg, 100 mg/kg, 120 mg/kg, 140 mg/kg, 160 mg/kg, or 180 mg/kg.

In one embodiment, the dosing regimen during the course of treatment includes a "loading dose" and a "maintenance dose." The therapy may be initiated with a "loading dose" (i.e., an initial higher dose of the drug that may be given at the beginning of the course of treatment before given a lower maintenance dose is given for a long period of time.) The maintenance dose may include 25%, 30%, 33%, 40%, 50%, 60%, 66%, 70%, 75%, 80% or more of the active ingredient contained in the loading dose.

In one embodiment, the dosing regimen during the course of treatment includes a loading dose, one or more "step-down" dose(s), and a maintenance dose. A "step-down" dose is a dosage in between the loading dose and the maintenance dose.

If administered intravenously, the rate of administration may vary depending on the concentration of the drug, the potency of the drug, and the characteristics of the patient. It is desirable that the rate of administration be sufficient to deliver a complete dose in a period ranging from 5 minutes to 1 hour, from 5 minutes to 45 minutes, from 10 minutes to 40 minutes, from 15 minutes to 35 minutes, from 5 minutes to 30 minutes, or from 10 minutes to 30 minutes. In one embodiment, the rate of administration may be approximately 0.2 mL/kg/min.

Administration of a composition or formulation can be once a month, once every other week, once a week, once a day, twice a day, or more often. Frequency may be decreased during a treatment maintenance phase of the treatment, e.g., once every other week instead of every week or every day. The dose and the administration frequency can be adjusted based on the judgment of the treating physician, for example taking into account the clinical signs, pathological signs and clinical and subclinical symptoms of a disease of the conditions treated with the present methods, as well as the patient's clinical history. For example, higher doses or frequency of administration, or a longer duration of treatment may be indicated when a patient is showing symptoms of GPA or a flare up of vasculitis, or if the patient has a history of previous GPA. Specific examples of dosage and frequency are provided in the Examples.

In one embodiment the dose administered will be rAAV hA1PI at dose levels comprised of vector genomes (VG)/kg body weight by intramuscular injection, subcutaneous injection, intravenous infusion or nebulized inhalation.

In one embodiment the dose administered will be a loading dose of the protein administered prior to use of the rAAV hA1PI at dose levels comprised of vector genomes (VG)/kg body weight by intramuscular injection, subcutaneous injection, intravenous infusion or nebulized inhalation.

Length of treatment, i.e., number of days, months, or years, will be readily determined by a physician treating the subject; however the number of days of treatment may range from about 1 day to about 365 days or more. For instance, the length of treatment of a loading dose may be the first administration only, or it may be a course of a once weekly dose for a period of two weeks to a month or more. A step-down treatment period after the initial loading dose can range anywhere from one weekly dose to a once weekly dose for 2 weeks, 3 weeks, 4 weeks, 5 weeks, 6 weeks, 7 weeks, 8 weeks, 9 weeks, 10 weeks, 11 weeks, 12 weeks, or more. Then a subsequent maintenance dosing period can range from one month, to 5, weeks, 6 weeks, 7 weeks, 9 weeks, 10 weeks, 11 weeks, 12 weeks, 13 weeks, 14 weeks, 15 weeks, 16 weeks, 18 weeks, 20 weeks, 24 weeks, 25 weeks, 28 weeks, 30 weeks, 6 months, 8 months, one year, two years, or more. In one embodiment, the length of the maintenance period may last for the rest of the patient's life span to suppress chronic symptoms or recurrence or flare up. In one embodiment, this lifelong treatment is A1PI supplementation therapy. As provided by the present methods, and discussed below, the efficacy of treatment can be monitored during the course of treatment to determine whether the treatment has been successful, or whether additional (or modified) treatment is necessary.

As used herein the terms "therapeutically effective" and "effective amount", used interchangeably, applied to a dose or amount refer to a quantity of a composition, compound or pharmaceutical formulation that is sufficient to result in a desired activity upon administration to a subject in need thereof.

Within the context of the present invention, the term "therapeutically effective" refers to that quantity of a composition, compound or pharmaceutical formulation that is sufficient to reduce, eliminate or delay at least one symptom of a disease or condition specified herein, e.g., GPA. When a combination of active agents is administered, the effective amount of the combination, or individual agents, may or may not include amounts of each agent that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

As used herein, "treating" or "treatment" of a state, disorder or condition (e.g., GPA) includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; and/or (2) inhibiting the state, disorder or condition, including arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

Treating can include inhibiting the levels of c-ANCA or inhibiting the binding of c-ANCA to PR3, or inhibiting the activation of neutrophils by PR3, or inhibiting the degranulation of neutrophils in a subject for at least a predetermined time frame in the subject. For example, a predetermined time frame may be, e.g., at least one week, at least two weeks, at least three weeks, at least 1 month, at least 2 months, at least 3 months, at least 4 months, at least 5 months, at least 6 months, at least 7 months, at least 8 months, at least 9 months, at least 10 months, at least 11 months, or at least 12 months. In one embodiment, the predetermined time frame is at least 6 months.

Treating can include inhibiting vasculitis in a subject. When vasculitis is inhibited, the Birmingham Vasculitis Activity Score Modified for Wegener's Granulamatosis (BVAS for WG) is decreased for at least a predetermined time frame. For example, a predetermined time frame may be, e.g., at least one week, at least two weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 2 years, at least 3 years or more. In one embodiment, the predetermined time frame is at least 6 months.

Treating can include inhibiting the number or severity of disease flare-ups in a subject. In one embodiment, the number or severity of disease flare ups are decreased by at least 25%, by at least 30%, by at least 35%, by at least 40%, by at least 50%, by at least 60%, by at least 70%, by at least 75%, by at least 80%, or by at least 90% over a time period of at least one month, at least two months, at least three months, at least four months, at least five months, at least six months, at least seven months, at least eight months, at least nine months, at least 10 months, at least 11 months, or at least a year. In one embodiment, the decrease in severity or occurrence of flare ups is by at least 50% for at least six months.

Treating can include extending the period before relapse of GPA in a subject. For example, the extension may be for a predetermined time frame by e.g., at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 2 years, at least 3 years or more. In one embodiment, the predetermined time frame is at least 6 months.

Further, treating can mean a decrease in occurrence or severity of one or more of the following symptoms: Joint pain without obvious swelling; joint inflammation; documented temperature elevation, e.g., oral temperatures (38.0° C.) (not attributed to other causes), Petechiae (small red spots), palpable purpura, or ecchymoses (large plaques) in skin or oozing (in the absence of trauma) in the mucous membranes; extensive tissue necrosis due to severe ischemia (e.g., digit); mouth ulcers (not attributed to other causes); mouth conjunctivitis; mouth episcleritis; retro-orbital mass/proptosis; uveitis; scleritis; retinal exudates (excluding hard exudates); retinal haemorrhages; bloody nasal discharge; nasal crusting; nasal ulceration (not due to trauma); tenderness or pain over paranasal sinuses or X-ray evidence of sinusitis; nasal bridge collapse; swollen salivary glands; subglottic inflammation; conductive deafness; deafness caused by damage to the auditory nerve or cochlea; pericarditis; mesenteric ischemia (Defined as severe abdominal pain, bloody diarrhea, gut perforation/infarction); pleurisy; chest nodules or cavities (new); Pseudotumour or ulceration of tracheobronchial tree (excluding those caused by tumors or infections); alveolar haemorrhage; dyspnea requiring artificial ventilation; hematuria without RBC casts (≥1+ on urinalysis; ≥10 rbc/hpf); RBC casts in urinary sediment; rise in creatinine >30% or creatinine clearance fall >25%; meningitis (Severe headache+/−neck stiffness, ascribed to inflammatory meningitis after the exdusion of infection, bleeding, and other causes); stroke; spinal cord lesion; cranial nerve palsy, sensory peripheral neuropathy (e.g., glove or stocking distribution of sensory loss); motor mononeuritis multiplex; weight loss (>2 kg over 28 day period not attributed to other causes); seizures; genitourinary involvement; cardiac valvular lesions; cutaneous infarctions (splinter hemorrhages, digital infarcts); pulmonary infiltrates (not due to alveolar hemorrhage, cavity); loss of pulses/threatened loss of limb; angina; cardiomyopathy; pancreatitis; or aural D/C. Again, the decrease in occurrence or severity of these symptoms may occur over a predetermined time frame, e.g., at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 2 years, at least 3 years or more. In one embodiment, the predetermined time frame is at least 6 months.

The decrease in severity or occurrence may be a decrease in comparison to the same subject or group of subjects over a given time period or in comparison to a subject or group of subject who has not been administered the present compositions.

In one embodiment, the PR3 inhibitor is administered alone. In another embodiment, the PR3 is administered in combination with another pharmaceutically active agent or therapeutic. In one embodiment, the pharmaceutically active agent or therapeutic is a corticosteroid, such as prednisone, hydrocortisone, hydrocortisone acetate, cortisone acetate prednisolone, methylprednisolone, and variants thereof. In another embodiment, the additional active agent is cyclophosphamide, methotrexate or azothiprine.

Compositions and formulations including a PR3 inhibitor ("agent") as described herein can be administered orally, topically, or parenterally, or by any other suitable methods known in the art. The term "parenteral" includes injection or deposition or sustained release via vehicles or devices (e.g., intravenous, subconjunctival, subtenon, episcleral, intrascleral, subscleral, intraperitoneal, epidural, intrathecal, intramuscular, intraluminal, intratracheal, epidermal, intradermal, subdermal or subcutaneous). Moreover, the different agents administered in the combination therapy disclosed herein may be administered by different routes. For example, a PR3 inhibitor disclosed herein may be injected intravenously, injected subcutaneously, inhaled, or in some formulations, taken orally.

While it is possible to use an agent disclosed herein for therapy as is, it may be preferable to administer the agent as a pharmaceutical formulation, e.g., in admixture with a suitable pharmaceutical excipient, diluent, or carrier selected with regard to the intended route of administration and standard pharmaceutical practice. Pharmaceutical formulations include at least one active compound, in association with a pharmaceutically acceptable excipient, diluent, and/or carrier.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A composition disclosed herein may further comprise one or more pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

A composition disclosed herein may further comprise one or more pharmaceutically acceptable carriers. Pharmaceutically acceptable carriers useful in the immunogenic compositions disclosed herein include any compatible agent that is nontoxic to an individual at the dosages and concentrations employed, and has substantially no long term or permanent detrimental effect when administered and encompasses terms such as pharmacologically acceptable vehicle, stabilizer, solubilizer, diluent, additive, auxiliary or excipient. Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. A carrier disclosed herein may also act as an adjuvant. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4th edition 2003).

It will be appreciated that the amount of an agent disclosed herein required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. In one embodiment, the active agent is administered in combination with a glucocorticoid, such as prednisone or prednisolone. Preliminary doses can be determined according to animal tests, and the scaling of dosages for human administration can be performed according to art-accepted practices.

In certain embodiments, the present disclosure provides kits for treating GPA in a subject. The kits can include the PR3 inhibitor disclosed herein. The skilled artisan will appreciate that the dosages of the above PR3 inhibitors may be varied without departing from the nature of the present disclosure, and thus other dosages are also encompassed by the present disclosure. The skilled artisan will know which dosages of the PR3 inhibitors disclosed herein may be safely and effectively administered to a subject according to the standard of care and knowledge in the art, and can include the PR3 inhibitors described herein.

In a specific embodiment, a kit includes the PR3 inhibitory composition disclosed herein. In certain embodiments, the kit is for treating GPA. The kit can further optionally include instructions for use. The kit can further optionally include (e.g., comprise, consist essentially of, consist of) syringes or applicators preloaded with the above mentioned agents and/or vials containing one or more of the agents.

The kits, regardless of type, will generally include one or more containers into which the biological agents (e.g., inhibitors) are placed and, preferably, suitably aliquotted. The components of the kits may be packaged either in aqueous media or in lyophilized form.

Many of the present inhibitors of PR3, in particular the protein or peptide inhibitors, may be made by conventional means, such as recombination. In addition, the present inhibitors may be isolated from mammalian (including human) plasma or made by the body's own cells through viral transfection.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Flames et al., eds. (1999) Protein Expression: A Practical Approach. Oxford University Press Oxford; Freshney (2000) Culture of Animal Cells: A Manual of Basic Technique. 4th ed. Wiley-Liss; among others. The Current Protocols listed above are updated several times every year.

The present compositions include DNA or RNA sequences encoding the protein or peptide PR3 inhibitors described herein, including DNA or RNA sequences encoding antibodies or antibody fragments.

The term "recombinant" as used herein refers to a polypeptide produced through a biological host, selected from a mammalian expression system, an insect cell expression system, a yeast expression system, and a bacterial expression system.

Accordingly, the nucleic acid molecules disclosed herein may be incorporated in a known manner into an appropriate expression vector which ensures good expression of the proteins of the invention. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The present specification therefore contemplates a recombinant expression vector of the invention containing a nucleic acid molecule encoding a protein or peptide PR3 inhibitor, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β1-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β1-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the proteins of the invention may be expressed in prokaryotic cells, such as *Escherichia coli* (Zhang et al., Science 303 (5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153: 163 (1983), and Cullen et al. (Bio/Technology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Lucklow, V. A., and Summers, M. D., Virology 170:31-39 (1989)).

Alternatively, the proteins of the invention may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins of the invention may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2 (4): 212-22 (1996)) or synthesis in homogenous solution (Houbenweyl, Methods of Organic Chemistry, ed. E. Wansch, Vol. 15 I and II, Thieme, Stuttgart (1987)).

Patients having detectable levels of ANCA and A1PI deficiency resulting in damage to the lungs may benefit from augmentation therapy. Augmentation therapy is intravenous infusions, usually weekly, of alpha-1 antitrypsin protein purified from healthy plasma donors. The goal is to increase the level of alpha-1 protein in the blood and lungs in order to slow or stop the progression of Alpha-1 lung disease. In patients also having detectable levels of ANCA, the increase in A1PI would effectively cleave all PR3 receptors on circulating neutrophils in GPA patients. Augmentation therapy is prepared from pooled human blood plasma that has been screened for hepatitis A, B, and C and tested for HIV as well as other infectious viruses. Additional antiviral procedures are used by all manufacturers during the purification process. Of the side effects that have been reported, headaches, muscle and joint pain, and temporary flu-like symptoms are the most frequent complaints.

Aspects of the present specification can also be described as follows:

1. A method for treating vasculitic syndrome comprising administering a composition comprising a Proteinase 3 (PR3) inhibitor to a patient in need thereof.
2. The method according to embodiment 1, wherein the PR3 inhibitor is administered weekly or bi-weekly.
3. The method according to embodiment 1 or 2, wherein the PR3 inhibitor is produced by the patient following viral transfection.
4. The method according to any one of embodiments 1-3, wherein the PR3 inhibitor is administered systemically.
5. The method according to any one of embodiments 1-4, wherein the PR3 inhibitor is administered by inhalation, enterally or parenterally.
6 The method according to any one of embodiments 1-5, wherein the PR3 inhibitor is administered intravenously, by inhalation, orally, intramuscularly, intraarterially, nasally, intracardiac, subcutaneously, or transmucosally.
7. The method according to any one of embodiments 1-6, wherein PR3 inhibitor is α-1 Protease Inhibitor (A1PI), Serpin B1, Trappin-2, elafin, Eglin c, a modified α-1 antichymotrypsin, α-2 macroglobulin, or azapeptides or a PR3 antibody or antibody fragment thereof.
8. The method according to embodiment 7, wherein the antibody or antibody fragment is selected from the group consisting of a monoclonal antibody, polyclonal antibodies, chimeric antibodies, an Fc region of an antibody, a full-length heavy chain of an antibody, a full-length light chain of an antibody, a variable region of an antibody, a CDR (1, 2, or 3) of an antibody.
9. The method according to any one of embodiments 1-6, wherein the PR3 inhibitor is a 1,2,5-thiadiazolidin-3-one 1,1 dioxide derivative, an N-hydroxysuccinimide derivative, 7-$NH_2$-4-CI-3-(2-bromoethoxy)isocoumarin, 3,4-dichloroisocoumarin, MeO-Suc-Ala-Ala-Pro-$Val^P(OPh)_2$, Boc-Val-Pro-$Val^P(OPh)_2$, MeO-Suc-Ala-Ala-Pro-$ValCh_2CI$, or N-tosy-L-phenylalanine-chloromethyl ketone (TPCK).
10. The method according to embodiment 7, wherein the A1PI having an amino acid sequence of SEQ ID NO: 1 with the addition of VRSP at the C-terminal, or amino acids 1-306 of SEQ ID NO: 1, or a sequence having an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 1, amino acids 1-359 of SEQ ID NO: 1 with the addition of VRSP at the C-terminal, or amino acids 1-306 of SEQ ID NO: 1 or a sequence having an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 1, amino acids 1-359 of SEQ ID NO: 1 with the addition of VRSP at the C-terminal, or amino acids 1-306 of SEQ ID NO: 1.

11. The method according to embodiment 7 or 10, wherein the A1PI has at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 1, amino acids 1-359 of SEQ ID NO: 1 with the addition of VRSP at the C-terminal, or amino acids 1-306 of SEQ ID NO: 1 or has, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or non-contiguous amino acid deletions, additions, and/or substitutions relative to SEQ ID NO: 1, amino acids 1-359 of SEQ ID NO: 1 with the addition of VRSP at the C-terminal, or amino acids 1306 of SEQ ID NO: 1.

12. The method according to any one of embodiments 7, 10 or 11, wherein the A1PI has one or more of the following amino acid changes to SEQ ID NO: 1: S4L, amino acid 12 is deleted, L23P, D26H, D26A, T37A, H39L, A58T, L61P, R63C, L65P, S69F, amino acid 75 is deleted, S75F, A84T, G91E, T92I, T96A, T109M, P112T, 1116N, R125H, G139S, G139D and N140G, G172R, G172W, Q180E, T174H, amino acids 190-198 are change from QGKIVDVLK to GFQNAILVR, E228K, E229D, V237A, T273N, D280V, D280G, E288V, amino acid 305 is deleted, V326I, S354F, A360T, D365N, E366K, M382R, P386H, P386T, E387K, P393L, E400D, G410L, N414S, and P415H.

13. The method according to embodiment 7, wherein the Serpin B1 having an amino acid sequence of SEQ ID NO: 2, or a sequence having an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 2 or a sequence having an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 2.

14. The method according to embodiment 7 or 13, wherein the Serpin B1 has at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 2 or has, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or non-contiguous amino acid deletions, additions, and/or substitutions relative to SEQ ID NO: 2.

15. The method according to any one of embodiments 7, 13 or 14, wherein the Serpin B1 comprises an amino acid sequence modified at of F343-C344 and/or C344-M345 of SEQ ID NO: 2.

16. The method according to any one of embodiments 7 or 13-15, wherein the Serpin B1 has SEQ ID NO: 3 deleted or contains up to 3 amino acid substitutions in SEQ ID NO: 3

17. The method according to any one of embodiments 7 or 13-16, wherein SEQ ID NO: 3 of SEQ ID NO: 2 is substituted with SEQ ID NO: 4, SEQ ID NO: 5, SEQ ID NO: 6, SEQ ID NO: 7 or SEQ ID NO: 8.

18. The method according to embodiment 7, wherein the Trappin-2 having an amino acid sequence of SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9, or a sequence having an amino acid sequence identity of, e.g., at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9, or a sequence having an amino acid sequence identity of, e.g., at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9.

19. The method according to embodiment 7 or 18, wherein the Trappin-2 has at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9, or has, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or noncontiguous amino acid deletions, additions, and/or substitutions relative to SEQ ID NO: 9, amino acids 26-117 of SEQ ID NO: 9, amino acids 35-117 of SEQ ID NO: 9, amino acids 61-117 of SEQ ID NO: 9, amino acids 31-47 of SEQ ID NO: 9, or amino acids 55-71 of SEQ ID NO: 9.

20. The method according to any one of embodiments 7, 18 or 19, wherein the Trappin-2 has an amino acid substitution at amino acids 17, 34, 91, and 92 of SEQ ID NO: 9.

21. The method according to any one of embodiments 7 or 18-20, wherein the Serpin B1 has up to 4 of the following amino acid amino acid substitutions to SEQ ID NO: 9: T17M, T34P, R91C, or C92A.

22. The method according to embodiment 7, wherein the azapeptide is SEQ ID NO: 12, SEQ ID NO: 13, SEQ ID NO: 14 or SEQ ID NO: 15.

23. The method according to embodiment 7, wherein the PR3 antibody or antibody fragment thereof binds an epitope present in the amino acid sequence of SEQ ID NO: 11 or amino acids 28-248 of SEQ ID NO: 11, or an epitope present in a sequence have at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 11 or amino acids 28-248 of SEQ ID NO: 11, or n epitope present in a sequence have at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99% sequence identity to SEQ ID NO: 11 or amino acids 28-248 of SEQ ID NO: 11.

24 The method according to embodiment 7 or 23, wherein the PR3 antibody or antibody fragment thereof binds an epitope having at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, contiguous and/or non-contiguous amino acid deletions, additions, and/or substitutions relative to SEQ ID NO: 11 or amino acids 28-248 of SEQ ID NO: 11, or binds an epitope having at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, contiguous and/or non-contiguous amino acid deletions, additions, and/or substitutions relative to SEQ ID NO: 11 or amino acids 28-248 of SEQ ID NO: 11.

25. The method according to any one of embodiments 7, 23 or 24, wherein the PR3 antibody or antibody fragment thereof binds to an epitope present in amino acid sequence of 28-248 of SEQ ID NO: 11.

26. The method according to any one of embodiments 7 or 23-25, wherein the PR3 antibody or antibody fragment thereof binds to an epitope present in amino acid sequence of SEQ ID NO: 11 having one or more of the following amino acid substitutions or deletions: A2R, S38I, P40PI, Q46E, R48A, S64D, A70P, V119I, A135T, T136S, or amino acid 255 is deleted.

27. The method according to any one of embodiments 1-26, wherein the composition further comprises a pharmaceutically acceptable carrier.

28. The method according to any one of embodiments 1-27, wherein the treatment results in an inhibition or reduction of vasculitis, the levels of c-ANCA, the activation of neutrophils, or the degranulation of neutrophils.

29. The method according to any one of embodiments 1-28, wherein the vasculitic syndrome includes, without limitation, granulomatosis with polyangiitis (GPA or Wegener's Granulomatosis), small vessel vasculitides, microscopic polyangiitis, pauci-immune crescentic glomerulonephritis, Churg-Strauss syndrome, drug induced vasculitides, cystic fibrosis, inflammatory bowel disease, primary sclerosing cholangitis, rheumatoid arthritis, autoimmune liver disease, drug induced syndromes or a parasitic infection.

30. The method according to any one of embodiments 1-29, wherein the treatment results in a reduction in the Birmingham Vasculitis Activity Score Modified for Wegener's Granulamatosis (BVAS for GPA), an inhibition or reduction of disease flare-ups, an extension of the period before relapse, or a decrease in the occurrence or severity of one or more of: Joint pain without obvious swelling; joint inflammation; documented temperature elevation, Petechiae, palpable purpura, ecchymoses in skin or oozing in the mucous membranes; extensive tissue necrosis due to severe ischemia; mouth ulcers (not attributed to other causes); mouth conjunctivitis; mouth episcleritis; retro-orbital mass/proptosis; uveitis; scleritis; retinal exudates; retinal haemorrhages; bloody nasal discharge; nasal crusting; nasal ulceration; tenderness or pain over paranasal sinuses; X-ray evidence of sinusitis; nasal bridge collapse; swollen salivary glands; subglottic inflammation; conductive deafness; deafness caused by damage to the auditory nerve or cochlea; pericarditis; mesenteric ischemia; pleurisy; chest nodules or cavities; Pseudotumour or ulceration of tracheobronchial tree; alveolar haemorrhage; dyspnea requiring artificial ventilation; hematuria without RBC casts; RBC casts in urinary sediment; rise in creatinine >30% or creatinine clearance fall >25%; meningitis; stroke; spinal cord lesion; cranial nerve palsy, sensory peripheral neuropathy; motor mononeuritis multiplex; weight loss; seizures; genitourinary involvement; cardiac valvular lesions; cutaneous infarctions; pulmonary infiltrates; loss of pulses/threatened loss of limb; angina; cardiomyopathy; pancreatitis; or aural D/C.

31. The method according to any one of embodiments 1-30, wherein the treatment results in an inhibition of, reduction of, or decrease of one or more symptoms for a period of at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 2 years, or at least 3 years or more.

32. The method according to any one of embodiments 1-31, wherein the dose of PR3 inhibitor administered weekly ranges from 1-1000 mg/kg, 1-500 mg/kg, 1-200 mg/kg, 1-100 mg/kg, 1-50 mg/kg, 10-500 mg/kg, 10-250 mg/kg, 10-200 mg/kg, 10-150 mg/kg, 10-100 mg/kg, 10-50 mg/kg, 50-1000 mg/kg, 50-500 mg/kg, 50-250 mg/kg, 50-200 mg/kg, 50-150 mg/kg, 50-100 mg/kg, 20-500 mg/kg, 20-250 mg/kg, 20-200 m/kg, 20-150 mg/kg, 20-100 mg/kg, or 20-60 mg/kg.

33. The method according to any one of embodiments 1-32, wherein the dose administered daily ranges from 0.05 μg/kg to 5 mg/kg, 0.1 pg/kg to 5 mg/kg, 1 μg/kg to 5 mg/kg, 50 μg/kg to 5 mg/kg, 0.1 mg/kg to 5 mg/kg or 1 mg/kg to 5 mg/kg, 34. The method according to any one of embodiments 1-33, wherein the dose administered ranges from $1.0\times 10^{9}$ to 1.0×102020 vector genomes (VG)/kg body weight.

35. A kit comprising a PR3 inhibitor as described in any one of embodiments 1-34 and vials containing the PR3 inhibitor or preloaded syringes or applicators.

36. Use of a composition comprising a PR3 inhibitor as described in any one of embodiments 1-34 in the treatment of a vasculitic syndrome.

37. A composition comprising a PR3 inhibitor as described in any one of embodiments 1-34 for use in the treatment of a vasculitic syndrome.

38. Use of a composition comprising a PR3 inhibitor as described in any one of embodiments 1-34 in the manufacture of a medicament for the treatment of a vasculitic syndrome.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Cell Based Assays

Proteinase 3 (PR3)-processed IL-113 activity is blocked by plasma A1PI (Sigma Aldrich, Cat #A9024, also called AAT) in human A549 cells (a model for serine protease activity, ATCC® CCL-185™). Human A549 cells were stimulated in PR3-preincubated precursor interleukin-113 (pro IL-113, Sigma Aldrich, Animal-component free, recombinant, expressed in *E. coli,* ≥98% (SDS-PAGE), ≥98% (HPLC), cell culture tested) in the presence of increasing concentrations of plasma derived A1PI overnight.

On the following day the cell culture medium was harvested and IL-6 measured by ELISA (Thermo Scientific, Human IL-6 ELISA Kit).

Figure 2:
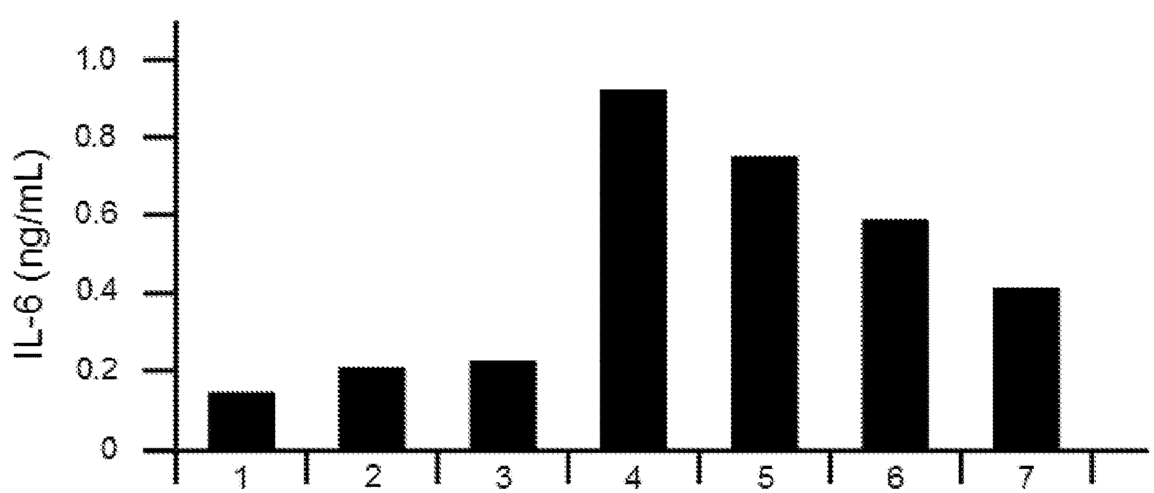
FIG. 2 depicts a bar graph showing A1PI inhibition of IL-6 production in a dose-dependent manner.

A1PI significantly decreased IL-6 production in a dose-dependent manner (Table 1, FIG. 2). When compared to the control, cultures treat with PR3 or precursor interleukin-113 showed negligible stimulation of IL-6 production (control 0.15 ng/ml of IL-6 verses 0.21 ng/mL and 0.23 ng/ml of IL-6 production for PR3 and pro IL-1 (3, respectively). As expected, culture treated with both PR3 or precursor interleukin-1 (3 exhibited a significant increase in IL-6 production (0.92 ng/ml). However, treatment of cultures with increasing amounts of A1PI showed a dose-dependent decrease in IL-6 production (Table 1). The normal physiologic range of serum A1PI is approximately 80 mg/dL or 800,000 ng/mL. As such, these results have physiological relevance.

TABLE 1

A1PI inhibition of IL-6 production in a dose-dependent manner.

| Experiment | PR3 | Pro IL-1β | A1PI | IL-6 |
|---|---|---|---|---|
| Control | — | — | — | 0.15 mg/mL |
| PR3 | 33 ng | — | — | 0.21 ng/mL |
| Pro IL-1β | — | 100 ng | — | 0.23 ng/mL |
| Test 1 | 33 ng | 100 ng | 0 ng/mL | 0.92 ng/mL |
| Test 2 | 33 ng | 100 ng | 500 ng. mL | 0.75 ng/mL |
| Test 3 | 33 ng | 100 ng | 1000 ng/mL | 0.59 ng/mL |
| Test 4 | 33 ng | 100 ng | 2000 ng/mL | 0.42 ng/mL |

Example 2

Cytotoxicity Assay

A cell culture provides a model of the blood vessels by using HUVEC (human umbilical vein endothelial cells) cultured to 80-90% confluence as a representation of the blood vessel wall. The following is a model of GPA in cell culture using HUVEC and human blood neutrophils that are primed and activated by c-ANCA in the same manner as the disease. HUVEC are sensitized to inflammatory damage by pre-exposure to BCNU and ionomycin. In the disease state of Granulomatosis with Polyangiitis (GPAANegener's), activated neutrophils attack the blood vessel walls. This study evaluated two compounds, A1PI (α-1-antitrypsin; Sigma Aldrich Cat. No. A9024, lot SLBL9794V, 90% purity) and elafin (AnaSpec Cat. No. AS-61641, lot 1360190, 95% purity), and their ability to mitigate the induced damage to HUVEC as a model of the vascular endothelium compared to the negative control al-antichymotrypsin (Athens Research & Technology, Cat. No. 16-16-012400, lot AX2014-02, >95% purity). al-Antichymotrypsin was chosen as a negative control due to its structural similarity to A1PI and lack of activity against the PR3 receptor. α-1-Antichymotrypsin inhibits neutrophil cathepsin G and mast cell chymase.

Confluent HUVEC was labeled with calcein-AM as a fluorescent marker. Calcein-AM is a cell-permeant dye that can be used to determine cell viability in HUVEC (and most eukaryotic cells). In live cells the non-fluorescent calcein AM is converted to a green-fluorescent calcein upon uptake after acetoxymethyl ester hydrolysis by intracellular esterases. Calcein-AM dye requires very small quantities of cells while maintaining the same sensitivity as the traditional $^{51}$Cr assay. Once taken up by the cell, free calcein is generally membrane impermeable and only permeates through gap junctions. Although there is some leakage over the incubation period, this is accounted for through the use of a control of HUVEC alone, labelled with Calcein-AM and used to determine the baseline fluorescence level accounting for normal cellular processes.

Peripheral blood neutrophils were primed to enhance expression of the PR-3 receptor (proteinase 3) with 50 U/mL TNF. A high proportion of membrane PR3 positive neutrophils is a risk factor for the development of vasculitis, and elevated membrane PR3 levels are associated with a higher relapse rate in patients with Wegener granulomatosis. Activated neutrophils were then added ($5\times10^5$ neutrophils/well) to plated calcein labeled HUVEC to produce an inflammatory response. Four dose concentrations of A1PI (0.25, 0.5, 1.0 and 2.0 mg/mL) and one dose of elafin (0.25 mg/mL) were evaluated for prevention of the activation of neutrophils and lysis of the cells. One dose concentration of the negative control al antichymotrypsin (0.25 mg/mL) was evaluated.

Three a-PR-3 MoAbs [monoclonal antibodies (15 μg/mL of α-PR3 WGM2 and 5 μg/ml each of a-PR3 4A5 and α-PR 6A6, for a total of 25 μg/mL)] were added to activate the neutrophils to attack the HUVEC, causing lysis of the HUVEC. α-PR3 4A5 and α-PR3 6A6 clones were obtained from Eurodiagnostica and the α-PR3 WGM2 from Abcam. These 3 clones were selected to provide a model of the polyclonal response that would be seen in vivo and represent three binding sites on the PR-3 receptor (Van Der Geld, Characterization of monoclonal antibodies to PR3 as candidate tools for epitope mapping or human anti-PR3 autoantibodies, 1999). After addition of the activated neutrophils, test compounds and α-PR3 mAbs, cells were incubated for 4 hours at 37° C. Following incubation the supernatant was evaluated for fluorescence. When neutrophils attack the HUVEC and cell lysis occurs, the fluorescent calcein label is released from damaged membranes and measured in the supernatants.

A1PI and elafin showed a functional response with the negative control al antichymotrypsin failing to provide a meaningful change in fluorescence release (Table 2). A1PI provided a response that was dose dependent and directional in nature. The mean fluorescence was determined from 3×100 pL aliquots of supernatant from each well, with 6 wells for each condition (18 replicates total). HUVEC lysed with a detergent provided criteria for 100% release. Fluorescence assays were performed using a TECAN Genios reader and Magellan software.

TABLE 2

HUVEC Cell Culture Assay

| Experiment | PR3 Inhibitor | α-PR3 mAbs | Mean | Std. Dev. | % CV | % Release |
|---|---|---|---|---|---|---|
| No Treatment | – | + | 4339.3 | 335.1 | 7.7 | 21.1 |
| No Treatment | – | – | 5849.7 | 545.1 | 9.3 | 0.2 |
| Negative K | – | + | 4417.7 | 612.2 | 10.9 | 21.9 |
| Test 1 | 0.25 mg/mL A1PI | + | 4937.0 | 372.4 | 6.4 | 14.1 |
| Test 2 | 0.5 mg/mL A1PI | + | 5387.8 | 202.5 | 3.5 | 7.2 |
| Test 3 | 1.0 mg/mL A1PI | + | 5750.0 | 557.9 | 10.4 | 1.7 |
| Test 4 | 2.0 mg/mL A1PI | + | 5804.0 | 519.3 | 8.9 | 0.9 |
| Test 5 | 0.25 mg/mL Elafin | + | 5455.7 | 329.6 | 6.0 | 6.2 |

Example 3

Treatments of GPA Using a PR3 Inhibitor

A patient complains of bleeding from the nasal passage and after a complete physical and diagnostic tests, a physician diagnoses him with GPA. The patient has normal A1PI levels yet also has detectable levels of c-ANCA, with frequent flare-ups. The patient is administered exogenous A1PI intravenously at 60 mg/kg/week for a period six months. His symptoms, such as bleeding from the nasal passage, are reduced after six months of treatment and the GPA is considered to be "in remission." This reduction in a GPA symptom indicates successful treatment with a pharmaceutical composition disclosed herein.

A patient complains of bleeding from the nasal passage and after a complete physical and diagnostic tests, a physician diagnoses him with GPA. The patient has normal A1PI levels yet also has detectable levels of c-ANCA, with frequent flare-ups. The patient is administered an initial loading dose of exogenous A1PI intravenously at 180 mg/kg, and a week later is administered exogenous A1PI at 120 mg/kg/week for a period of seven weeks. He is subsequently dosed with exogenous A1PI at 60 mg/kg/week for a period of 16 weeks. His symptoms, such as bleeding from the nasal passage, are reduced after one month of treatment and subsequent flare ups are suppressed during the treatment. Flare ups are suppressed for a period after discontinuing treatment ceases. This reduction in a GPA symptom indicates successful treatment with a pharmaceutical composition disclosed herein.

A patient complains of bleeding from the nasal passage and after a complete physical and diagnostic tests, a physician diagnoses him with GPA. The patient has normal A1PI levels yet also has detectable levels of c-ANCA. The patient is administered an initial loading dose of exogenous A1PI intravenously at 120 mg/kg/week for four weeks. He is subsequently dosed with exogenous A1PI at 60 mg/kg/week for a period of 20 weeks. His symptoms, such as bleeding from the nasal passage, are reduced after one month of treatment. This reduction in a GPA symptom indicates successful treatment with a pharmaceutical composition disclosed herein.

A patient complains of difficulty in breathing and after a complete physical and diagnostic tests, a physician diagnoses him with GPA due to detectable levels of ANCA and A1PI deficiency resulting in damage to the lungs. An augmentation therapy of a-1 antitrypsin protein is prepared from pooled human blood plasma of healthy plasma donors that has been screened for hepatitis A, B, and C and tested for HIV as well as other infectious viruses. Additional antiviral procedures are used by during the purification process. Weekly intravenous infusions a-1 antitrypsin protein are administered to the patient. His symptoms, such as difficulty in breathing, are reduced after one month of treatment. This reduction in a GPA symptom indicates successful treatment with a pharmaceutical composition disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," 'Third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of or "consisting essentially of" in lieu of or as an amended for "comprising." When used in the claims, whether as filed or added per amendment, the closed-ended transitional phrase "consisting of excludes any element, limitation, step, or feature not expressly recited in the claims. The closed-ended transitional phrase "consisting essentially of limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of is being defined as only including those elements, limitations, steps and/or features specifically recited in the claim whereas the meaning of the closed-ended transitional phrase "consisting essentially of is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method for treating Granulomatosis with Polyangiitis (GPA) in a patient in need thereof comprising administering a therapeutically effective amount of a Proteinase 3 (PR3) inhibitor to the patient, wherein administration inhibits a physiological function of PR3, thereby treating GPA, wherein the PR3 inhibitor is selected from elafin, Trappin-2, Eglin c, α-1 antichymotrypsin, and α-2 macroglobulin.

2. The method according to claim 1, wherein the PR3 inhibitor is administered weekly or bi-weekly.

3. The method according to claim 1, wherein the PR3 inhibitor is administered systemically.

4. The method according to claim 1, wherein the PR3 inhibitor is administered by inhalation, enterally or parenterally.

5. The method according to claim 1, wherein the PR3 inhibitor is administered intravenously, by inhalation, orally, intramuscularly, intraarterially, nasally, intracardiac, subcutaneously, or transmucosally.

6. The method according to claim 1, wherein the PR3 inhibitor is administered at one of the following doses: 1-1000 mg/kg, 1-500 mg/kg, 1-200 mg/kg, 1-100 mg/kg, 1-50 mg/kg, 10-500 mg/kg, 10-250 mg/kg, 10-200 mg/kg, 10-150 mg/kg, 10-100 mg/kg, 10-50 mg/kg, 50-1000 mg/kg, 50-500 mg/kg, 50-250 mg/kg, 50-200 mg/kg, 50-150 mg/kg, 50-100 mg/kg, 20-500 mg/kg, 20-250 mg/kg, 20-200 mg/kg, 20-150 mg/kg, 20-100 mg/kg, or 20-60 mg/kg.

7. The method according to claim 6, wherein the PR3 inhibitor is administered weekly at 50 to 500 mg/kg.

8. The method according to claim 6, wherein the PR3 inhibitor is administered weekly at 50 to 250 mg/kg.

9. The method of claim 1, wherein the administering comprises administering a loading dose and a maintenance dose of the PR3 inhibitor.

10. The method of claim 9, wherein the loading dose is administered weekly or bi-weekly.

11. The method of claim 9, wherein the loading dose is administered weekly at a dose of 50 to 150 mg/kg.

12. The method of claim 9, wherein the maintenance dose is administered weekly.

13. The method of claim 9, wherein the maintenance dose comprises 25% to 80% of the PR3 inhibitor of the loading dose.

* * * * *